United States Patent [19]
Mitchell et al.

[11] Patent Number: 5,354,289
[45] Date of Patent: Oct. 11, 1994

[54] ABSORBENT PRODUCT INCLUDING SUPER ABSORBENT MATERIAL AND A FLUID ABSORPTION CAPACITY MONITOR

[75] Inventors: Winalee G. Mitchell, Perrysburg; Andrew J. Szypka, Curtice; Michael Plotka, Waterville, all of Ohio

[73] Assignee: Principle Business Enterprises Inc., Dunbridge, Ohio

[21] Appl. No.: 96,552

[22] Filed: Jul. 23, 1993

[51] Int. Cl.$^5$ .................. A61F 13/15; A61F 13/20
[52] U.S. Cl. .................. 604/361; 604/358; 604/368; 604/385.1
[58] Field of Search ............... 604/358, 361, 362, 368, 604/385.1

[56] References Cited

U.S. PATENT DOCUMENTS

| | | | |
|---|---|---|---|
| 4,192,311 | 3/1980 | Felfoldi | 604/361 |
| 4,507,121 | 3/1985 | Leung | 604/361 |
| 4,743,238 | 5/1988 | Colon et al. | 604/361 |
| 4,834,733 | 5/1989 | Huntoon et al. | 604/361 |
| 5,219,341 | 6/1993 | Serbak et al. | 604/361 |
| 5,266,928 | 11/1993 | Johnson | 604/361 |

Primary Examiner—Randall L. Green
Assistant Examiner—P. Zuttarelli
Attorney, Agent, or Firm—David C. Purdue; John C. Produe

[57] ABSTRACT

A capacity monitor for diapers and the like, including super absorbent material disposed in or adjacent to an absorbent core is disclosed. The monitor comprises an indicator and a baffle to prevent direct contact between the absorbent core and the indicator. The indicator is preferably a ribbon of hot melt adhesive with a wetness indicator which changes color when exposed to liquid. The baffle is a substantially water impervious sheet positioned between the absorbent core and the indicator so as to prevent direct contact between them. The diaper and the monitor are constructed so that there is a threshold level of liquid which, when deposited in the diaper, will effect a color change in the indicator. A quantity of liquid which is below the threshold will not effect a color change in the indicator and a quantity of liquid which is above the threshold will effect a color change in the indicator. In the latter case, the indicator will change color over a portion of its length which is proportional to the quantity of deposited liquid which exceeds the threshold amount. The threshold is preferably at least twenty percent of the in-situ capacity of the super absorbent material in the diaper. In a diaper comprising an absorbent core, a backing sheet and a cover sheet, the monitor is positioned between the absorbent core and the backing sheet and, preferably, a strip of non-woven material is positioned between the monitor and the backing sheet to prevent sticking.

12 Claims, 4 Drawing Sheets

ABSORBENT PRODUCT INCLUDING SUPER ABSORBENT MATERIAL AND A FLUID ABSORPTION CAPACITY MONITOR

BACKGROUND OF THE INVENTION

1. Field of the Invention

This invention relates to the field of absorbent products including super absorbent polymers, especially for use by persons with urinary incontinence. More specifically, the invention relates to such products including a sensor or monitor which provides an indication when the absorption capacity of the super absorbent polymer has been exceeded.

2. Description of the Prior Art

There are numerous examples of wetness indicating devices which have been proposed for use in diapers and other absorbent products for use by persons with urinary incontinence. One example of a wetness indicator is represented by a class of hot melt adhesive products which include a wetness indicating component. U.S. Pat. Nos. 4,743,238, 5,035,691, 5,066,711 and 5,089,548 disclose various hot melt adhesives with wetness indicators, many of which would be suitable for use in a capacity monitor according to the present invention. These hot melt products are in wide use in disposable diapers today. In conventional use, they are applied in the form of a narrow straight bead, a thin ribbon or a spiral bead to a water impervious backing sheet and are in direct contact with, and in liquid communicable relation with, an absorbent layer of fluff. Tests conducted on several commercially available disposable diaper products including such conventionally applied hot melt adhesives with wetness indicators demonstrate that the wetness indicators provide a positive indication of wetness, i.e., a color change in the hot melt, when no more than 15 milliliters of a 0.9% NaCl solution was deposited thereon. Even 5 milliliters of such solution was sufficient to effect a color change in some of the conventional applied hot melt adhesives with wetness indicator. The color change occurred over relatively short lengths, i.e., between ¼ inch and 2 and ½ inches, of the beads or ribbons of hot melt adhesive with wetness indicator at the low volume levels of 5 to 15 milliliters.

U.S. Pat. No. 3,731,685 discloses a moisture indicating strip which is designed for use with diapers and other absorbent products. One end of the strip is attached to the inside of the diaper or the like and the other end, which is impregnated with a color change chemical, extends out of the diaper. Liquid is transported by capillary action from inside the diaper or the like to the color change chemical outside the diaper.

U.S. Pat. No. 3,759,261 discloses diapers having a layer with a pattern printed thereon and one or more layers which mask the pattern when dry. When wetted, the masking layers no longer mask the pattern which becomes visible through a backing sheet, thereby providing a wetness indicating function.

U.S. Pat. No. 3,952,746 discloses a humidity indicator strip incorporated in a diaper including a water impervious backing sheet. A portion of the strip extends through an opening formed in the backing sheet.

U.S. Pat. No. 4,022,211 discloses a diaper including a wetness indicator comprising a layer of water soluble or water dispersible coloring agent applied to the water impervious backing sheet. When dry, the coloring agent is clearly visible through the backing sheet but, when wetted, the coloring agent is dispersed and is no longer visible through the backing sheet.

U.S. Pat. No. 4,231,370 discloses a wetness indicator in a diaper structure. The wetness indicator is positioned between a water impervious backing sheet and an absorbent core and comprises a flexible pH-change/-color-change coating which is preferably applied to the backing sheet and visible therethrough. The preferred coating material comprises first and second latexes, an acid buffer and bromo-phenol blue.

U.S. Pat. No. 4,287,153 discloses a diaper including a saline water indicating material positioned between a backing sheet and an absorbent core, and visible through the backing sheet. The preferred indicating material comprises a water-insoluble polymeric ion exchanger and a water-insoluble polymeric exchanged ion indicator in intimate contact with each other.

U.S. Pat. No. 4,507,121 discloses a diaper including a wetness indicator comprising a color change chemical which is isolated from the absorbent portions of the diaper so as to prevent contact between a wearer of the diaper and the color change chemical. Means are provided for supporting one way capillary action to transport liquid from the absorbent portions to the indicator to trigger the color change.

U.S. Pat. No. 4,704,108 discloses a wetness indicator comprising two metal strips incorporated in a diaper and circuitry for detecting changes in the electrical conductivity in absorbent portions of the diaper due to the presence of moisture therein.

U.S. Pat. No. 4,705,513 discloses a wetness indicator for diapers. The indicator comprises indicia printed in waterproof ink on a paper carrier strip. The paper strip is positioned adjacent to a water impervious backing sheet and the indicia is masked by the strip so long as it remains dry. When wetted, the carrier strip no longer masks the indicia and it becomes visible through the backing sheet to indicate wetness.

U.S. Pat. No. 4,738,674 discloses an absorbent product including a moisture indicator which provides an indication of wetness at a point remote from where liquid is actually deposited on the product. The indicator includes a wicking strip for transporting liquid from a point where it is deposited to an edge of the product where it contacts a moisture indicating substance which can provide a visual indication, such as a color change, that it has been wetted.

U.S. Pat. No. 4,834,733 discloses a diaper including an actuating member which shrinks when wetted and it is connected to an indicating mechanism so that, when moisture contacts the actuating member, it shrinks and displaces the indicating mechanism providing an indication that fluid has been deposited in the diaper.

U.S. Pat. No. 5,078,708 discloses a diaper comprising a transparent or translucent, water impervious backing sheet and an absorbent core. Opening are provided in the core so that urine or stools deposited in the diaper are visible through the backing sheet to indicate the need for a change.

Super absorbent materials have been incorporated in commercially available diapers and the like, for many years. U.S. Pat. No. 5,072,687, the disclosure of which is incorporated herein by reference, discloses several varieties of absorbent diaper products including super absorbent materials. Known super absorbents absorb large amounts of liquid and liquid absorbed in super absorbents can not be squeezed back out of the super absorbents. This is to be contrasted with fluff which is composed of cellulose or the like fibers. Fluff can absorb many times its weight in liquid but liquid absorbed in fluff can be squeezed back out of the fluff. In a diaper, squeeze out of urine from fluff can cause leakage and prolonged skin contact with urine soaked fluff can cause damage to healthy skin and inhibit healing of damaged skin.

Each super absorbent polymer has a "speed" which is used herein to mean the rate at which the super absorbent will absorb liquid. The speed of a super absorbent depends upon many factors including its composition, the quantity of liquid it has already absorbed and the amount of liquid available to be absorbed. For a given liquid, each super absorbent also has a "free swell capacity" which is used herein to mean the maximum amount of liquid which unrestrained super absorbent particles will ultimately absorb when exposed to an excessive amount of a liquid, i.e., one which far exceeds the capacity of the super absorbent relative to that liquid. A given super absorbent with a given capacity for a given liquid will have a different, somewhat lower capacity for that liquid when the super absorbent is contained in, for example, an absorbent core of a diaper. The term "in-situ capacity" will be used hereinafter to refer to the volume of a given liquid which is absorbed by super absorbent associated with an absorbent core containing at least one other, different absorbent material, such as fluff, within thirty minutes after the liquid is deposited slowly in a single spot in the absorbent core. The in-situ capacity of super absorbent in such an absorbent core does not include the capacity of the fluff or other absorbent material in the core; the term refers only to the capacity of the super absorbent to absorb a given liquid, under the recited conditions, within thirty minutes of the time the liquid is deposited.

Some super absorbents are fast and some are slow. In granular form, commercially available super absorbents take approximately one to three minutes to absorb their free swell capacity of water, when unrestrained and exposed to large amounts of water. When super absorbents are incorporated in absorbent cores with other absorbent materials, such as fluff, they absorb liquid more slowly than this, largely because they are in contact with less liquid. All super absorbents have a given speed when dry, and, as they absorb liquid, the speed and remaining capacity of the super absorbent decreases.

Figure 1:
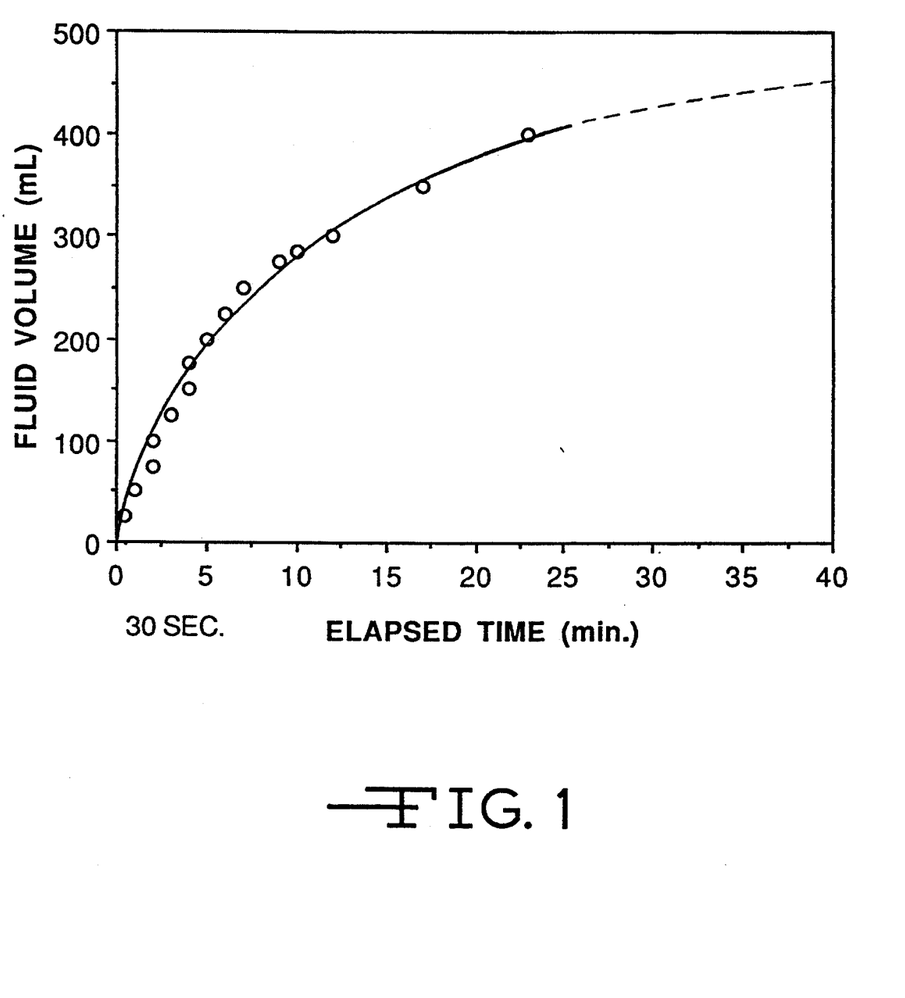
FIG. 1 is plot of elapsed time before a prior art diaper including super absorbent material achieves a zero skin wetness number, versus quantity of liquid deposited in the diaper.

Some of the characteristics discussed in the preceding paragraph are illustrated in FIG. 1 in respect of super absorbents contained in absorbent fluff cores in diapers. FIG. 1 is a plot of data collected from tests made of a commercial version of several medium sized SlimLine ® diapers manufactured by Principle Business Enterprises, Inc. In the test, many different quantities of a 0.9% NaCl solution were deposited on SlimLine medium size diapers. For each quantity of solution, the diapers were tested for skin wetness at different intervals of time after the solution was deposited. In the skin wetness test, a medium size SlimLine diaper was placed, with its water impervious backing sheet facing downwardly, on a level surface. In the center of the diaper, a given quantity of a 0.9% NaCl solution was deposited at the rate of 7.0 milliliters per second. Absorbent paper toweling, cut into three inch by five inch rectangles, was stacked, the stack was weighed and its dry weight was recorded. At various time intervals after the 0.9% NaCl solution had been deposited on the diaper, a previously weighed stack of paper toweling was placed on top of the diaper and a three inch by five inch, rectangularly shaped five pound weight was placed on top of the paper toweling. After fifteen seconds, the weight was removed from the paper toweling and it was reweighed. The weight of the dry toweling was subtracted from the weight of the wet paper toweling to give a skin wetness number corresponding with the weight of 0.9% NaCl solution which was released by the diaper into the paper toweling. The time which elapsed before the skin wetness number was 0.0 grams for a given quantity of liquid was plotted for several different quantities of liquid and the results are shown in FIG. 1. The medium sized SlimLine diapers which were tested had 12 grams of Aridall 1465 super absorbent material, available from Chemdal, in the fluff layer. At relatively low volume levels, the speed of the super absorbent in the SlimLine diapers is relatively fast, as reflected by the steep slope of the plot on the left side of FIG. 1. At higher volume levels, the slope of the plot is not as steep and this reflects the well known phenomenon associated with super absorbents used in absorbent products, namely, the speed of a super absorbent material decreases as it absorbs liquid. As the capacity of the super absorbent is used up, the speed decreases and the slope of a plot like that shown in FIG. 1 approaches zero. It will be appreciated that the in-situ capacity of the super absorbent in a medium SlimLine diaper for synthetic urine is approximately 400 to 450 milliliters. The plot in FIG. 1 provides a good way to approximate in-situ capacity because, for example, the fluid volume of about 425 milliliters at thirty minutes elapsed is almost entirely absorbed within the super absorbent material, whereby the skin wetness number is 0.0 because the super absorbent does not release liquid under pressure. The volume of 285 milliliters associated with a skin wetness of 0.0 after ten minutes is significant, in terms of the medium SlimLine, because it is preferred that skin not be in contact with a diaper with skin wetness in excess of 0.0 for more than ten minutes.

In a SlimLine diaper, which comprises a substantial quantity of absorbent cellulose fluff (70 grams) as well as the 12 grams of super absorbent polymer, liquid is immediately absorbed into the fluff component and, over time, the liquid is withdrawn from the fluff and absorbed by the super absorbent polymer. So long as the in-situ capacity of the super absorbent is not exceeded by the quantity of liquid, the fluff layer will, within thirty minutes, dry out in the sense that it will preferentially give up absorbed liquid for absorption by the super absorbent polymer in the diaper.

It has been determined that urine absorbed in and held by super absorbent material in a disposable diaper is innocuous to a wearer and skin adjacent to and in contact with a diaper which contains urine held by super absorbent material (and no urine held in a fluff layer) is not damaged by such contact. This is true even for relatively large volumes of urine such as 100 or 200 milliliters. Prolonged exposure of skin to urine, either direct exposure to urine or exposure to urine which is absorbed in fluff, can damage healthy skin by causing a rash or other reaction while prolonged exposure of already damaged skin can inhibit healing and aggravate the damage to the skin.

As noted above, when only 15 milliliters of 0.9% NaCl solution is applied to commercially available diapers including conventionally applied hot melt adhesives with wetness indicators, the wetness indicators change color signalling the need for a change of the diaper. This was true, even for commercially available diapers which included super absorbent materials. It will be appreciated that such use of hot melt adhesives with wetness indicators in a SlimLine diaper, or other diaper including super absorbent material, would provide, in many cases, a premature indication of the need for a diaper change because:

1. it takes approximately two minutes for the super absorbent polymer in medium SlimLine diapers to completely absorb 100 milliliters of 0.9% NaCl solution (0.0 skin wetness) but the super absorbent has a remaining in-situ capacity to completely absorb, in ten minutes, another 200 milliliters of 0.9% NaCl solution;
2. in the two minutes that it takes for 100 milliliters of 0.9% NaCl solution to be absorbed out of the fluff into the super absorbent, that quantity of 0.9% NaCl solution in the fluff would trigger a color change in conventionally applied hot melt adhesives with wetness indicators.

While this phenomenon might increase sales of SlimLine diapers and other products incorporating conventionally applied hot melt adhesives with wetness indicators, it would also unnecessarily increase the burden on already overburdened landfills as well as the burden on care givers who tend to the changing of absorbent products used by persons with urinary incontinence. So, there is demonstrated a need for a capacity monitor which is capable of providing a reliable indication of when the in-situ capacity of super absorbent material has been exceeded, without providing a premature indication, such as when there is substantial remaining in-situ capacity in the super absorbent.

SUMMARY OF THE INVENTION

The instant invention is based upon the discovery of a capacity monitor which is operable to provide a visible signal when the in-situ capacity of super absorbent material in a given absorbent core has been, or is close to being, exceeded by liquid absorbed in the absorbent core. In a diaper comprising a water impervious backing sheet and an absorbent core comprising fluff and super absorbent material, the monitor comprises an indicator, such as a hot melt adhesive with a wetness indicator between the absorbent core and the backing sheet. The monitor further comprises a substantially water impervious baffle positioned between the absorbent core and the hot melt adhesive, to prevent substantial contact between the indicator and liquid contained in the absorbent core, except when the quantity of such liquid exceeds a predetermined threshold volume of liquid. The monitor may further comprise a strip of non-woven material, or the like, positioned between the indicator and the backing sheet to prevent sticking therebetween. When a quantity of liquid which exceeds the threshold volume of liquid is deposited in the diaper, some of the liquid will migrate around the baffle and trigger a color change or the like in the indicator. The threshold level is predetermined, for a given diaper, relative to the in-situ capacity of the super absorbent material in the absorbent core of the diaper. Preferably, the threshold volume is at least 20% of the in-situ capacity of the super absorbent. More preferably, the threshold is at least 30% of the in-situ capacity while 40% is more preferred still. In some cases, the threshold may approach or even exceed the in-situ capacity of the super absorbent in the absorbent core, if the other absorbent material therein is adequate to take up the slack.

When a strip of non-woven material, or the like, is provided between the indicator and the backing sheet, it facilitates the transfer of liquid from the core to the indicator so that a change in the indicator occurs reliably when the threshold amount is exceeded, thereby overcoming any tendency of the indicator to stick to the backing sheet and prevent a change in the indicator. In cases where the threshold is substantially below the in-situ capacity of the super absorbent, the monitor may further comprise printed indicia which provides a visually discernible signal which, together with the degree or extent or length indicator which changes color or the like, provides an indication of the remaining in-situ capacity, if any, of the super absorbent material in the absorbent core.

DETAILED DESCRIPTION OF THE INVENTION

Figure 2:
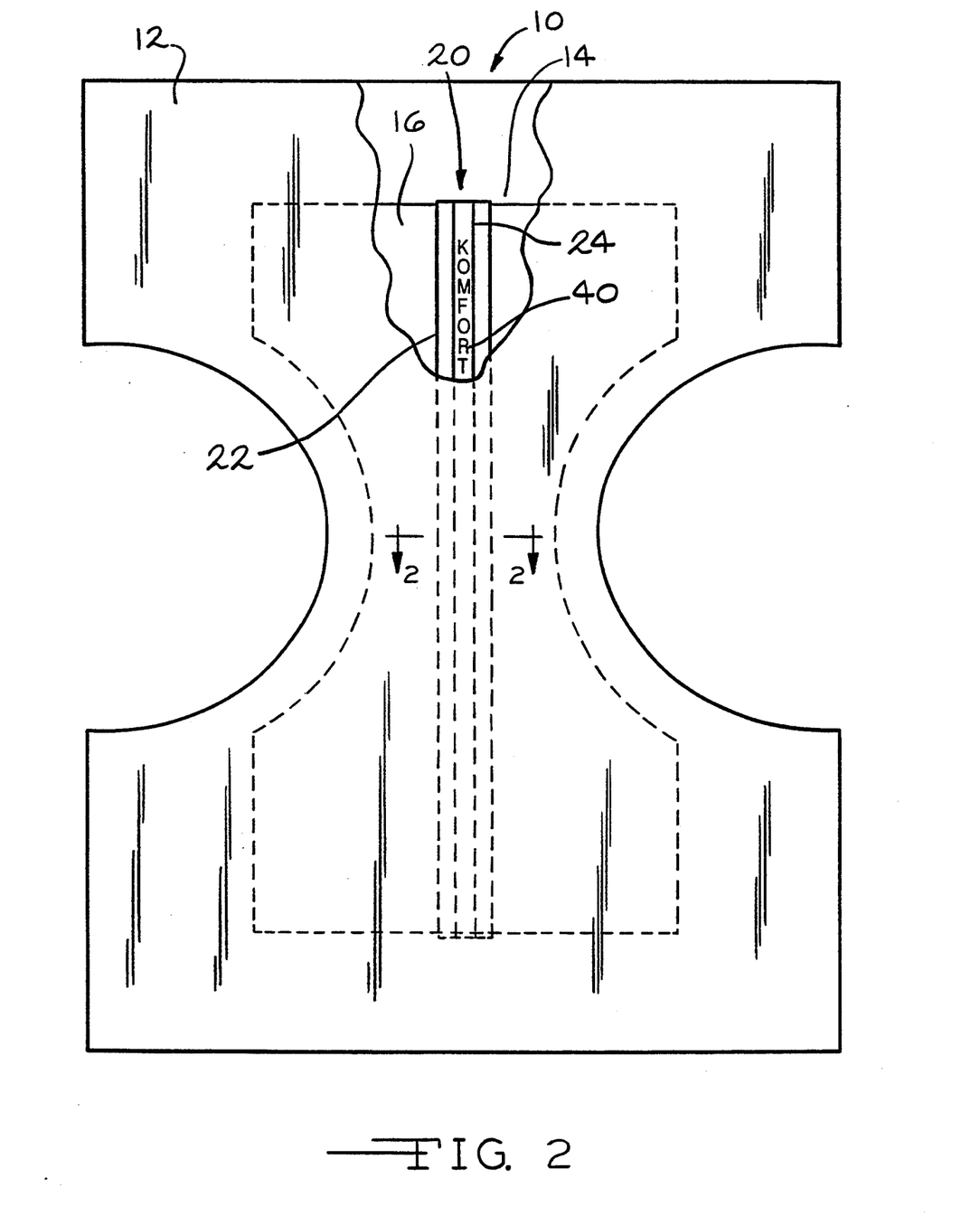
FIG. 2 plan view, partially broken away, of a diaper incorporating a capacity monitor according to the present invention.

Referring now to FIG. 2, a disposable diaper is indicated generally at 10. The diaper 10 comprises a water impervious backing sheet 12, a non-woven facing sheet 14 which would contact a wearer's skin when the diaper 10 is in use and an absorbent core 16. In accordance with the invention, the absorbent core has at least two absorbent components, which are illustrated in and discussed below in connection with FIG. 3. Specifically, the core 16 has an absorbent fluff component and a super absorbent component. In accordance with the present invention, the super absorbent may be incorporated into the absorbent core in any suitable manner including those disclosed in said U.S. Pat. No. 5,072,687. The patent discloses the deposition of particulate super absorbent into a fluff layer or batt. Also disclosed is a construction wherein super absorbent is contained in a laminate, i.e., one or more sheets of tissue with super absorbent adhered to and supported thereon, and the laminate is incorporated in an absorbent core. A combination of these constructions is also disclosed where loose super absorbent particles and laminate containing super absorbent are combined with an absorbent cellulose fluff bait. These components of diaper 10 are conventional and are well known in the industry.

A portion of the water impervious backing sheet 12 has been cut away in FIG. 2 to illustrate a capacity monitor, according to the present invention, indicated generally at 20. The monitor 20 comprises a baffle 22 which extends along the longitudinal centerline of the diaper 10 and an indicator 24 which undergoes a visually perceptible change when wetted. The indicator 24 is positioned between the backing sheet 12 and the absorbent core 16. The baffle 22, in turn, is positioned between the absorbent core 16 and the indicator 24. The baffle 22 is operable to prevent contact between liquid held in the absorbent core 16 and the indicator 24. The monitor 20 is constructed, however, so that when there is quantity of liquid in the absorbent core which approaches or exceeds the in-situ capacity of the super absorbent in the absorbent core, the some of the liquid will contact the indicator 24 effecting a perceptible change in it. Further details of construction for the diaper 10 as well as the capacity monitor 20 are discussed below with reference to FIG. 3.

Figure 3:
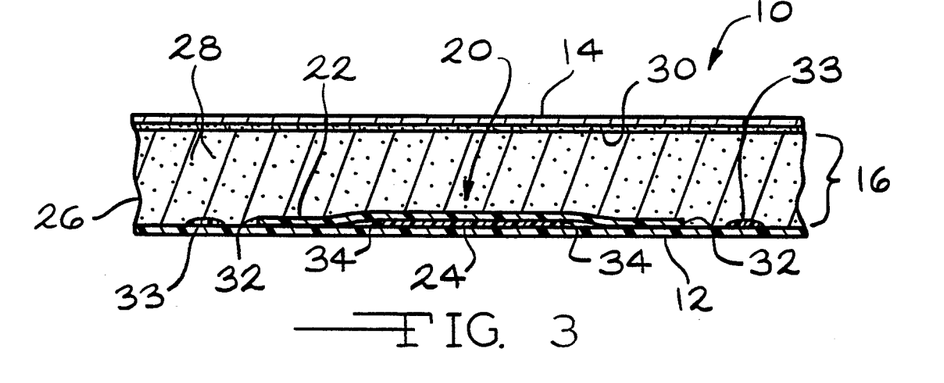
FIG. 3 is a cross sectional view, taken along the lines 3—3 of FIG. 2, showing some details of the capacity monitor according to the present invention.

The baffle 22 may comprises a sheet of polymeric, water impervious film or paper which has been treated or coated to render it water impervious or substantially so. The baffle 22 is positioned between the absorbent core 16 and the water impervious backing sheet 12. The core 16, as previously indicated, includes a fluff component 26 and a super absorbent component which, in the illustrated embodiment, comprises discreet particles of super absorbent 28 carried in the fluff 26. A layer of tissue 30 is positioned between the fluff 26 and the nonwoven facing sheet 14. As disclosed in U.S. Pat. No. 5,072,687, a layer of laminate (not shown) may be substituted for the tissue layer 30, or combined with it and positioned between the fluff layer 26 and the tissue layer 30. The monitor 20 further comprises the indicator 24 which is positioned between the baffle 22 and the water impervious backing sheet 12. The baffle 22 physically separates the fluff layer 26 and the absorbent core 16 from the indicator 24 so that there is no direct contact between the indicator 24 and the fluff layer 26 or the absorbent core 16.

The baffle 22 is comprised, at least in part, of a hydrophobic material so that it constitutes a physical barrier to the flow of liquid from the fluff layer 26 through the baffle 22 to the indicator 24. With the baffle 22 in place, liquid in the fluff layer 26 can reach the indicator 24 only if it travels around free edges 32 of the baffle and travels between the baffle 22 and the water impervious backing sheet 12 to reach the indicator 24. So long as the volume of liquid in the diaper is such that the liquid can be held tightly or fairly tightly in the absorbent components of the absorbent core 16, the liquid will not reach the indicator. When the volume of liquid in the diaper exceeds the volume which the absorbent components of the core 16 can hold fairly tightly, there will be excess liquid in the diaper 10 such as would tend to pool or puddle adjacent to or on the surface of the backing sheet 12 near the baffle 22 and some of it would travel around the free edges 32 of the baffle 22 and reach the indicator. In other words, there is a threshold level of liquid which must be deposited on the absorbent core in order for any liquid to reach the indicator. Thus, the movement of liquid from the absorbent core 16 to the indicator 24 is enabled when there is enough liquid. The edges 32 of the baffle 22 are free edges in the sense that they are not adhered to the backing sheet 12. Care must be taken, in producing a diaper with a capacity monitor 20 according to the invention in case the diaper includes conventional lines of hot melt adhesive without a wetness indicator 33 to adhere the absorbent core 16 to the backing sheet 12. Such adhesive lines 33 must not completely adhere the free edges 32 of the baffle 22 to the backing sheet 12, or vice versa. Instead, the hot melt adhesive lines 33 would be positioned, as shown in FIG. 3, where they do not engage the free edges 32 of the baffle 22.

The indicator 24 preferably comprises a hot melt adhesive with a wetness indicator. A preferred indicator material is NICOL-MELT 82525 which is available through Swift Adhesives or its parent Reichhold Chemical. This particular hot melt material is translucent and has a yellow color when it is applied, for example, to the baffle 22 or the water impervious backing sheet 12. In the illustrated embodiment, it is preferred that the indicator consist of a ribbon of the indicated hot melt adhesive with wetness indicator having a width of approximately one quarter to one half inch (0.5 to 1.5 centimeters) and a thickness of about one mil (0.025 millimeter). Insofar as the operability of the present invention is concerned, the indicator may be applied either to the backing sheet 12 or the baffle 22. Upon contacting most liquids, including synthetic and non-synthetic urine, the NICOL-MELT will change color, at the contact areas, from a light or hint translucent yellow to a relatively dark and deep blue. This color change is readily perceivable through the water impervious cover 12 which, as previously mentioned, is transparent or translucent.

The baffle 22 has a width which exceeds the width of the indicator 24. Consequently, free edge portions 32 of the baffle 22 overlap edges 34 of the indicator 24, thereby hindering liquid in the absorbent core 16 from traveling to the indicator 24. Good results have been obtained with a coated paper baffle having a width of approximately one and one quarter inches (3 centimeters) and an indicator having a width of about one quarter inch, so that at least one half inch (1.25 centimeters) of the baffle overlapped the edge of the indicator on each side.

The indicator 24 comprising the hot melt adhesive with wetness indicator serves the color change function noted above and can also serve to secure the baffle 22 in the diaper 10 relative to the water impervious backing sheet 12 as well as the other components. However, the baffle 22 does not need to be adhered by an indicator 24 to the backing sheet 12; the absorbent core 16 is secured to the backing sheet 12, as by adhesive lines 33 and the baffle 22 could be held captive between the backing sheet 12 and the absorbent core 16. As previously noted, the overlapping, free edge portions 32 of the baffle 22 are not adhered to the backing sheet 12 so that liquid can travel from the absorbent core 16, between the baffle 22 and the backing sheet 12 and reach the indicator 24.

In accordance with the invention, the diaper components just described cooperate to determine, for a given diaper, the threshold level of liquid which will be effective to change the indicator 24. It will be appreciated that there is a wide range of thresholds which are encompassed by the broader aspects of the present invention. The threshold volume can be affected by controlling:

the degree of overlap of the free edges of the baffle;
  the identity and shape of the particular indicator;
  the identity and quantity of the super absorbent;
  details of construction of the absorbent component; and
  the amount and type of fluff, or the like, in the absorbent core.

Generally speaking, increasing the amount of overlap of the baffle 22 will increase the threshold level while decreasing the amount of overlap has the opposite effect. The threshold could be increased by incorporating a particularly fast super absorbent in the absorbent core. As previously indicated, it is preferred, in a diaper according to the present invention, to have a threshold of at least 20% of the in-situ capacity of the super absorbent in the diaper. A 30% threshold is more preferred while 40% is still more preferred. It will be appreciated that a threshold approaching or even exceeding the in-situ capacity of the super absorbent component could be operable in a diaper according to the present invention. Since the absorbent core of a diaper according to the invention includes another absorbent component, such as fluff, a capacity monitor could be incorporated in a diaper according to the invention having a threshold exceeding the in-situ capacity of the super absorbent if, for example, the fluff component could handle the excess volume of liquid. Regardless of the threshold value of a particular combination of diaper and monitor, if the threshold is exceeded, liquid will reach some portion of the indicator.

Prior art diapers which include super absorbent and fluff and further include hot melt adhesives with wetness indicators, do not have baffles corresponding with the baffle 24. Consequently, these diapers have minuscule thresholds of 5, 10 or 15 milliliters of synthetic urine. A quantity of liquid in excess of these minor thresholds will effect a change in the wetness indicators in the hot melt adhesive, indicating the need for a diaper change, even if the vast majority of the in-situ capacity of super absorbent material in the diapers is unused. It is estimated that the threshold of such prior art diapers is less than 5% of the in-situ capacity of super absorbent in the diapers. In contrast, a capacity monitor in a diaper according to the present invention has a threshold of at least 20% of the in-situ capacity of super absorbent in the diaper, although 30 to 40% thresholds are preferred.

EXAMPLES 1 and 2

Some medium SlimLine diapers were produced but were modified to include capacity monitors according to the invention. In all of the diapers tested, the indicator was a ribbon, approximately one quarter inch wide and one mil thick, of NICOL-MELT 82525 hot melt adhesive with wetness indicator. The baffles were made of paper which had been treated/coated to make it impervious to liquid. The baffles were one and one half inch wide. Indica was printed on the baffle paper and was visible through the indicator and the water impervious backing sheet. The indicia comprised the word "KOMFORT" in a repeating pattern extending down the center of the diaper, as indicated by the reference numeral 40. The letters were sized and positioned so that each word was four and one half inches long. The diapers had absorbent cores comprising 12 grams of Aridall super absorbent dispersed in 70 grams of cellulose fluff.

One such diaper was tested by depositing in it 0.9% NaCl solution at a rate of 7 milliliters per second, in 40 milliliter increments with a final increment of 45 milliliters. The increments were timed to be at least ten minutes apart and, ten minutes after each 40 milliliter deposit, the indicator 24 was observed for evidence of a change in color. The results of this test are set forth below:

| EXAMPLE | Total Volume of 0.9% NaCl incrementally deposited on diaper (milliliters) | Description of color change |
| --- | --- | --- |
| 1 | 40 | no color change |
| 1 | 80 | no color change |
| 1 | 120 | no color change |
| 1 | 160 | color change in ¼ inch length of indicator |
| 1 | 200 | color change in three ¼ inch lengths of the indicator |
| 1 | 240 | color change in three ¼ inch lengths of the indicator |
| 1 | 285 | color change in four ¼ inch lengths of the indicator |

Seven diapers produced as described above were similarly tested except that the 0.9% NaCl solution was deposited at a controlled rate in seven different quantities on seven different diapers. The results are set forth below:

| EXAMPLE | Total Volume of 0.9% NaCl deposited on diapers (milliliters) | Description of color change |
| --- | --- | --- |
| 2a | 40 | no color change |
| 2b | 80 | no color change |
| 2c | 120 | no color change |
| 2d | 160 | color change in two areas, about 1 inch length, each |
| 2e | 200 | color change in three areas, about 1 inch in length, each |
| 2f | 240 | color change in three areas, about 1 inch in length, each |
| 2g | 285 | color change in two areas, about 1 inch in length, each |

These tests demonstrate that the threshold of the capacity monitor which in the modified medium SlimLine diaper was between 120 and 160 milliliters, regardless of whether liquid was applied all at once or in spaced apart intervals. With one exception, these tests indicate that, once the threshold was exceeded, there was a color change in a portion of the indicator and the length of the affected portion was proportional to the volume of liquid which exceeded the threshold. In a diaper according to the invention, having a threshold which is significantly below the in-situ capacity of the super absorbent, indicia such as 40, having a predetermined length can be combined with the monitor so as to provide an indication of the remaining in-situ capacity (or other measure of capacity) when the threshold is exceeded. With reference to FIG. 2, the length of the repeating indicia 40 has been predetermined relative to a particular capacity of a diaper corresponding with Examples 1 and 2a–2g. The length of the indicia 40 was based upon the capacity of the diaper to retain synthetic urine with skin wetness of 0.0 after ten minutes which, as shown in FIG. 1, is about 285 milliliters. With a threshold of between 120 and 160 milliliters, exhaustion of the remaining capacity of the diaper (approximately 140 milliliters) will be associated with a color change in the indicator over approximately four and one half inches of its length. The indicia 40 provide a convenient measure of this length as well as a convenient way to ascertain, for example when substantially less than four and one half inches of the indicator has changed color, that the diaper still has substantial capacity to absorb additional synthetic urine and exhibit, ten minutes after the synthetic urine is deposited, skin wetness of 0.0.

Figure 4:
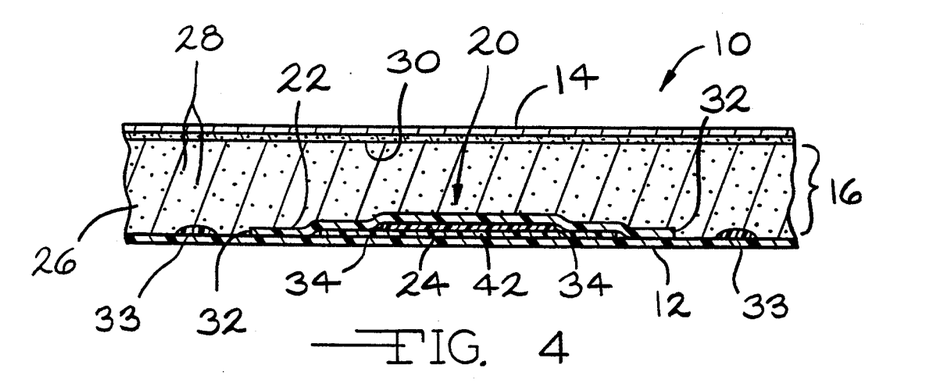
FIG. 4 plan view, partially broken away, of a preferred embodiment of a diaper incorporating a capacity monitor according to the present invention.

It has been determined that the hot melt adhesive with wetness indicator 24 (FIG. 3) can stick to the backing sheet 12 to such an extent that it prevents a change from occurring in the indicator 24, even when liquid in an amount exceeding the threshold amount is absorbed in the absorbent core. This problem is exacerbated by heat. It has further been determined that problems associated with sticking between the indicator 24 and the backing sheet 12 can be overcome in a preferred embodiment of the present invention which is described below with reference to FIGS. 4 and 5.

Figure 5:
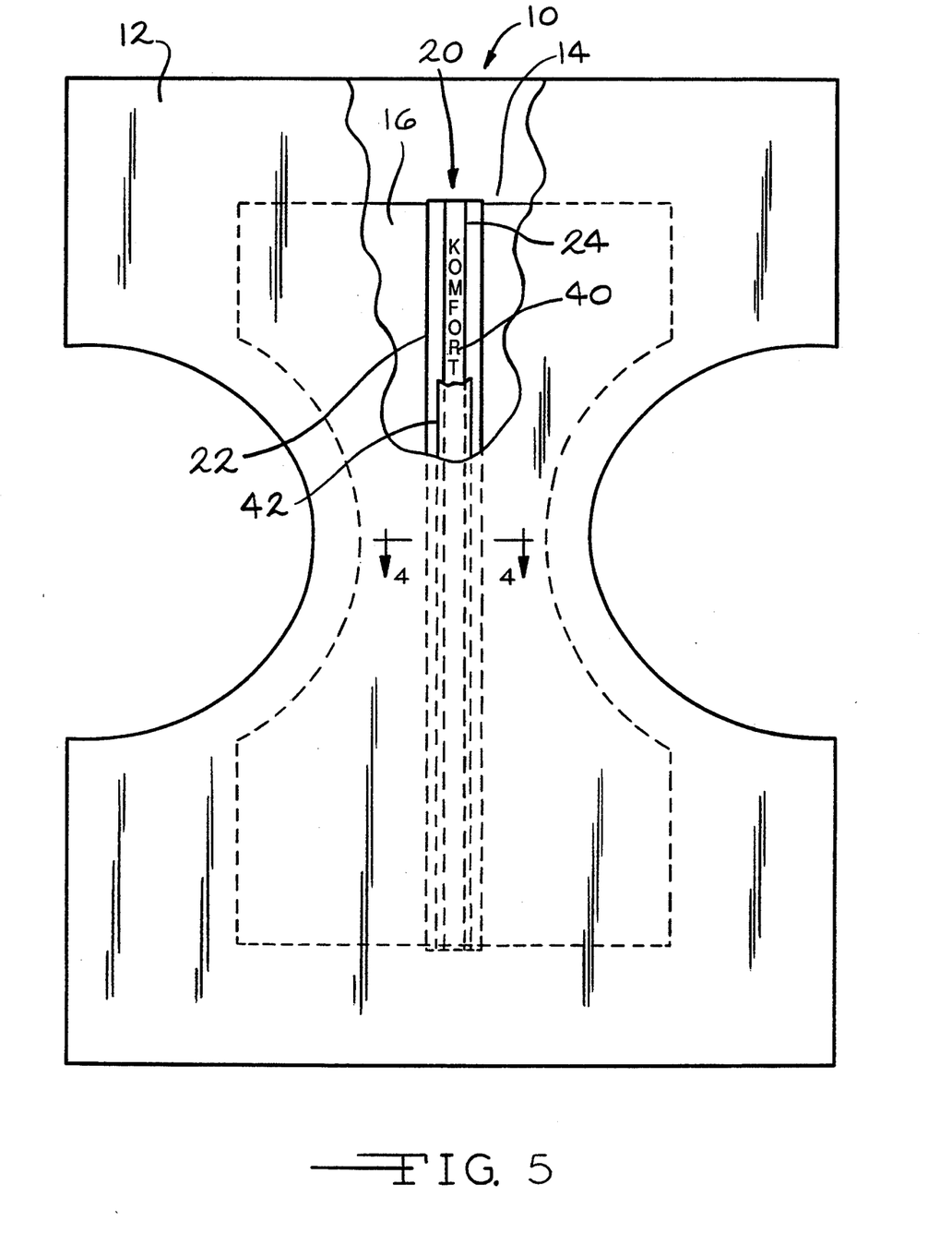
FIG. 5 is a cross sectional view, taken along the lines 5—5 of FIG. 4, showing some details of a preferred capacity monitor according to the present invention.

In a preferred embodiment, a comfort monitor indicated generally at 20' (FIGS. 4 and 5) includes a strip of non-woven material 42 positioned between the backing sheet 12 and the indicator 24. Preferably, as shown in FIG. 5, the width of the non-woven strip 42 is less than the width of the baffle 22, but is greater than the width of the indicator strip 24. Non-woven material is generally hydrophobic, meaning that it repels water and other liquids. In accordance with the preferred embodiment of the present invention, the non-woven strip 42 is treated with a surfactant (not shown) to make it hydrophilic. As a consequence, the treated non-woven strip can transmit liquid, when available, into contact with the indicator 24 to effect a color change in the indicator. This construction has been found to preserve the threshold properties discussed above, while ensuring that liquid, in an amount exceeding the threshold, will reach the indicator 24 and effect a change in it. Further, the strategic use of a hydrophilic strip of non-woven, or the like, as described above, prevents the indicator, when exposed to high temperatures, from sticking to the backing sheet 12 to such an extent that the monitor is rendered inoperable.

The foregoing description is intended to enable those skilled in the art to practice the present invention and constitutes the best mode presently known for practicing the invention. For example, although the invention has been described in the context of a diaper product, it will be appreciated that the invention has broader application to the field of products having an absorbent core including super absorbent polymer with a capacity monitor for indicating when a threshold amount of liquid has been absorbed in the core. Undoubtedly, modifications will occur to those skilled in the art, and such modifications may be resorted to without departing from the spirit and scope of the invention disclosed herein and claimed below.

We claim:

1. A diaper including a capacity monitor, said diaper comprising an absorbent core including super absorbent material, a hydrophilic cover sheet and a water impervious, translucent or transparent backing sheet, said core being positioned between said cover sheet and said backing sheet and said super absorbent material in said diaper having a given in-situ capacity for synthetic urine, said capacity monitor comprising
   an indicator extending longitudinally a substantial distance, said indicator being operable to provide a visually perceptible change when wet, said indicator being positioned in said diaper adjacent to said backing sheet so that the change of the indicator is visually perceptible through said sheet and
   a substantially water impervious baffle positioned inside the diaper between said backing sheet and said absorbent core so as to cover said indicator and separate it from said absorbent core, said baffle having a width which is greater than that of said indicator and a free edge around which synthetic urine can migrate from said absorbent core to said indicator, said baffle being operable to prevent the flow of synthetic urine into wetting relationship with said indicator when the diaper contains an amount of synthetic urine which is less than a given percent of the in-situ capacity of the super absorbent, and ineffective to prevent such flow when the diaper contains an amount of synthetic urine which is greater than the given percent of the in situ capacity of the super absorbent, the given percent being at least 20.

2. The diaper claimed in claim 1 which additionally includes
   indicia provided on said diaper and visible through said backing sheet, said indicia being operable to indicate a predetermined length of said indicator which undergoes a visually perceptible change when a quantity of synthetic urine approximately equal to the in-situ capacity of the super absorbent has been deposited on the diaper.

3. The diaper claimed in claim 1 or 2 wherein the given percent exceeds thirty percent of the in-situ capacity of the super absorbent in the diaper.

4. The diaper claimed in claim 1 or 2 wherein the given percent exceeds forty percent of the in-situ capacity of the super absorbent in the diaper.

5. A diaper including a capacity monitor, said diaper comprising an absorbent core comprising a fluff component and a super absorbent component, a hydrophilic cover sheet and a water impervious, translucent or transparent backing sheet, said core being positioned between said cover sheet and said backing sheet and said super absorbent material in said diaper having a given in-situ capacity for synthetic urine, said capacity monitor comprising
   an indicator extending longitudinally a substantial distance, said indicator being operable to provide a visually perceptible change when wet, said indicator being positioned in said diaper adjacent to said backing sheet so that the change of the indicator is visually perceptible through said backing sheet and
   a substantially water impervious baffle positioned inside the diaper between said backing sheet and said absorbent core so as to cover said indicator and separate it from said absorbent core, said baffle having a width which is greater than that of said indicator and a free edge around which synthetic urine can migrate from said absorbent core to said indicator, said baffle being effective, in cooperation with the components of the diaper, to prevent the flow of synthetic urine into wetting relationship with said indicator when the diaper contains an amount of synthetic urine which is less than a given percent of the in-situ capacity of the super absorbent, and ineffective to prevent such flow when the diaper contains an amount of synthetic urine which is greater than the given percent of the in situ capacity of the super absorbent, the given percent being at least 20.

6. The diaper claimed in claim 5 which additionally includes
   indicia provided on said diaper and visible through said backing sheet, said indicia being operable to indicate a predetermined length of said indicator which undergoes a visually perceptible change when a quantity of synthetic urine approximately equal to the in-situ capacity of the super absorbent has been deposited on the diaper.

7. The diaper claimed in claim 5 or 6 wherein the given percent exceeds thirty percent of the in-situ capacity of the super absorbent in the diaper.

8. The diaper claimed in claim 5 or 6 wherein the given percent exceeds forty percent of the in-situ capacity of the super absorbent in the diaper.

9. A diaper including a capacity monitor, said diaper comprising an absorbent core including a fluff component and a super absorbent component, a hydrophilic cover sheet and a water impervious, translucent or transparent backing sheet, said core being positioned between said cover sheet and said backing sheet and said super absorbent material in said diaper being operable to absorb up to a given, maximum quantity of a desired liquid to the extent that, ten minutes after deposition of said given amount of liquid, said diaper has a skin wetness number of substantially zero, said capacity monitor comprising a hot melt adhesive containing a color change indicator, and extending longitudinally a substantial distance, said indicator being operable to provide a visually perceptible color change when said hot melt adhesive is wet, said hot melt adhesive being positioned in said diaper adjacent to said backing sheet so that the change of color of the indicator is visually perceptible through said backing sheet and a substantially water impervious baffle positioned inside the diaper between said backing sheet and said absorbent core so as to cover said hot melt adhesive and separate it from said absorbent core, said baffle having a width which is greater than that of said hot melt adhesive and a free edge around which liquid can migrate from said absorbent core to said hot melt adhesive, said baffle cooperating with the components of the diaper to control the migration of liquid from said at least one absorbent component to said indicator so that said given quantity of desired liquid deposited on the diaper produces a visually perceptible change over a predetermined length of said indicator and indicia provided on said diaper and visible through said backing sheet, said indicia being operable to indicate the predetermined length of said hot melt adhesive which undergoes a visually perceptible change when said given quantity of desired liquid is deposited on the diaper.

10. An absorbent product including a capacity monitor, said product comprising an absorbent core including super absorbent material, said core having a first and a second side, and a water impervious, translucent or transparent backing sheet, said backing sheet being positioned adjacent to said first side of said core and said super absorbent material in said absorbent product having a given in-situ capacity for liquid, said capacity monitor comprising an indicator extending longitudinally a substantial distance, said indicator being operable to provide a visually perceptible change when wet, said indicator being positioned in said absorbent product between said backing sheet and said core so that the change of the indicator is visually perceptible through said backing sheet and a substantially water impervious baffle positioned inside the diaper between said backing sheet and said absorbent core so as to cover said indicator and separate it from said absorbent core, said baffle having a width which is greater than that of said indicator and a free edge around which liquid can migrate from said absorbent core to said indicator, said baffle being operable to prevent the flow of a liquid into wetting relationship with said indicator when the core contains an amount of the liquid which is less than a given percent of the in-situ capacity of the super absorbent, and ineffective to prevent such flow when the core contains an amount of the liquid which is greater than the given percent of the in situ capacity of the super absorbent, the given percent being at least 20.

11. The absorbent product claimed in claim 10 which further comprises a strip of non-woven material positioned between said indicator and said backing sheet, said strip of non-woven material being hydrophilic and being operable to prevent sticking between said indicator and said backing sheet so that liquid is able to migrate from said absorbent core to said indicator.

12. The diaper claimed in claim 1, 5 or 9 which further comprises a strip of non-woven material positioned between said indicator and said backing sheet, said strip of non-woven material being hydrophilic and being operable to prevent sticking between said indicator and said backing sheet so that synthetic urine is able to migrate from said absorbent core to said indicator.

* * * * *